US006925896B1

(12) United States Patent
Morton

(10) Patent No.: US 6,925,896 B1
(45) Date of Patent: Aug. 9, 2005

(54) METHOD OF COLLECTING CRIME SCENE EVIDENCE

(76) Inventor: Garrett D. Morton, 2813 E. Hills Dr., Lexington, KY (US) 40517

( * ) Notice: Subject to any disclaimer, the term of this patent is extended or adjusted under 35 U.S.C. 154(b) by 10 days.

(21) Appl. No.: 10/293,053

(22) Filed: Nov. 13, 2002

Related U.S. Application Data

(60) Provisional application No. 60/338,024, filed on Nov. 13, 2001.

(51) Int. Cl.[7] ............... G01N 1/04; A47K 7/02; B32B 3/02
(52) U.S. Cl. ............... 73/864.71; 15/215; 428/81
(58) Field of Search ............... 73/864.71; 15/215, 15/104; 283/68, 78

(56) References Cited

U.S. PATENT DOCUMENTS

| | | | | |
|---|---|---|---|---|
| 2,843,868 | A | * | 7/1958 | Borgstrom ............... 15/215 |
| 3,083,393 | A | * | 4/1963 | Nappi ............... 15/215 |
| 3,867,164 | A | * | 2/1975 | Orlando et al. ............... 401/267 |
| 4,144,760 | A | * | 3/1979 | Schlueter et al. ............... 73/864.71 |
| 4,706,600 | A | * | 11/1987 | Mason et al. ............... 118/31.5 |
| 4,713,274 | A | * | 12/1987 | Minor ............... 428/40.1 |
| 4,805,468 | A | * | 2/1989 | Choudhry ............... 73/864.71 |
| 4,811,444 | A | * | 3/1989 | Hamblin ............... 15/104.002 |
| 4,917,975 | A | * | 4/1990 | De Guzman ............... 428/81 |
| 5,114,188 | A | * | 5/1992 | Koch ............... 283/68 |
| 5,330,231 | A | * | 7/1994 | Godfrey ............... 283/78 |
| 5,390,680 | A | * | 2/1995 | Brenner ............... 600/592 |
| 5,511,594 | A | * | 4/1996 | Brennan et al. ............... 141/98 |
| 5,781,704 | A | * | 7/1998 | Rossmo ............... 706/45 |
| 6,494,489 | B2 | | 12/2002 | Massimo, Sr. |

FOREIGN PATENT DOCUMENTS

| | | | | | |
|---|---|---|---|---|---|
| EP | 353139 | A2 | * | 1/1990 | ............ A47G 27/02 |
| JP | 06090891 | A | * | 4/1994 | ............ A47L 23/22 |
| JP | 06169876 | A | * | 6/1994 | ............ A47L 23/22 |
| JP | 11195179 | A | * | 7/1999 | ............ G08B 15/00 |
| JP | 2001155264 | A | * | 6/2001 | ............ G08B 15/00 |

OTHER PUBLICATIONS

Web document: Lynn Peavey Company: "Tacky Mat" Sep. 2003 p. 1 of 1□□.*
Nano Times Corp: "Tacky Mat" information sheet 1998 pp. 1 and 2□□.*
Forensic Science Communications: "Trace Evidence Recoery Guidelines" vol. 1, No. 3, Oct. 1999 pp. 1-9□□.*

(Continued)

Primary Examiner—Hezron Williams
Assistant Examiner—John Fitzgerald
(74) Attorney, Agent, or Firm—King & Schickli, PLLC

(57) ABSTRACT

A method for recovering evidence from the footwear of a crime scene investigator is provided, comprising placing an adhesive evidence recovery sheet at an entryway to a crime scene, causing the crime scene investigator to step thereon upon exiting the crime scene, and covering the evidence recovery sheet with a protective cover. In this manner, evidence inadvertently adhering to the footwear of the investigator is removed and preserved for further analysis. In accordance with the method of this invention, a device for recovering evidence from the footwear of an investigator is provided, comprising an adhesive evidence recovery sheet and a protective cover. Adhesive strips on an obverse surface of the evidence recovery sheet prevent inadvertent dislodgement of the sheet from the floor surface on which it is placed.

14 Claims, 1 Drawing Sheet

OTHER PUBLICATIONS

Forensic Science Communications: "Hairs, Fibers, Crime, and Evidence" vol. 2, No. 3, Jul. 2000 pp. 1-6□□.*

ESD Systems.com, information sheet, "Tacky Mat" Mar. 2000, p. 1 of 1.*

Web document: Transolift ™ Print Lifters and Transheets ™, pp. 1-6, May 4, 2004.*

U.S. Department of Justice "Crime Scene Investigation: A Guide for Law Enforcement" Jan. 2000, pp. 1-48.*

Evident, Inc. Evidence Collection III: 1999, pp. 1-7.* www.CURTAIN-WALL.COM/cleanstep.htm; Jan. 25, 2003.

www.bassco.com/bbacess.html; Jan. 25, 2003.

* cited by examiner

METHOD OF COLLECTING CRIME SCENE EVIDENCE

This application claims the benefit of U.S. Provisional Patent Application Ser. No. 60/338,024 filed Nov. 13, 2001.

TECHNICAL FIELD

The present invention relates to methods for recovering evidence from crime scenes. In particular, the invention relates to a method and device for recovering evidence from the footwear of personnel investigating a crime scene. The method further relates to a method and device for preventing contamination of a crime scene by matter introduced to the scene from the footwear of investigating personnel.

BACKGROUND OF THE INVENTION

In a typical crime scene, numerous investigative personnel, such as police officers, crime laboratory personnel, and the like are involved in assessing the particulars of the crime and collecting evidence left by the perpetrators or victims. Evidence is likely to be found in any area and on any surface in a crime scene, such as on floors, carpets, furniture and walls.

Often, particular items of evidence such as clothing fibers, hairs, bodily fluids, and the like are so small as to be invisible to the eye, or are located on surfaces that render them difficult or impossible to detect, such as on non-contrasting carpet surfaces. In such cases, evidence crucial to the solution of the crime may go undetected. In addition, it is often the case that a crime scene investigator, during the course of the investigation, may inadvertently step on such undetectable items of evidence, and may transport such items on his or her footwear. A common solution utilized by crime scene investigators to collect difficult to detect items of evidence is to use "lifting tape," which is most commonly a roll of tape having a lower tack which can adhere to and lift fibers and the like for further processing. However, this does not solve the problem of evidence inadvertently removed from a crime scene on the footwear of an investigator.

Accordingly, there remains a need in the art for methods of collecting evidence, particularly difficult to detect evidence such as fibers, hair, fluids, and the like, inadvertently adhered to the footwear of crime scene investigators.

SUMMARY OF THE INVENTION

In accordance with the purposes of the present invention as described herein, a novel method for recovering evidence from the footwear of personnel investigating a crime scene is described. The method comprises placing an evidence recovery sheet having a low tack adhesive on at least one surface thereof in substantial proximity to at least one entryway to a crime scene. All personnel investigating the crime scene will be required to step on the low tack adhesive surface of the recovery sheet prior to exiting the crime scene. A protective cover may be placed over the evidence recovery sheet prior to transporting same to a laboratory for further analysis, thereby preserving the integrity of the evidence adhered thereto. It will be appreciated that in this fashion, any evidence, such as fibers, fluids, hairs, and the like, inadvertently contacted by the crime scene investigator's footwear, will adhere to the evidence recovery sheet, and may therefore be recovered for further investigation. In this way, loss of potentially valuable evidence is prevented in a simple, yet effective manner.

A plurality of evidence recovery sheets, placed in a vertically stacked orientation, may be placed in the crime scene entryway. As each investigator passes through the entryway to a crime scene and steps on the top-most evidence recovery sheet, it may be removed and covered with a protective cover. In this way, evidence removed from the footwear of a particular investigator may be keyed to that investigator during further analysis.

It should be appreciated that the present invention provides also a method for preventing crime scene contamination. An evidence recovery sheet may be placed in substantial proximity to an entryway to a crime scene, as described above, and all personnel entering the crime scene may be required to step on the sheet. In this way, dirt and debris may be removed from the investigator's footwear, thereby reducing the likelihood of inadvertent contamination of the crime scene.

The present invention also provides a device for recovering evidence from the footwear of personnel investigating a crime scene. The device of the present invention comprises an evidence recovery sheet having a low tack adhesive on at least one surface thereof, and a protective cover for covering the evidence recovery sheet to preserve the integrity of evidence adhered thereto. Low tack adhesives suitable for the purposes of the present invention, having sufficient adherent strength to remove fibers, fluids, and the like from footwear but allowing easy recovery of such evidence, are well known in the art. The protective cover may be similar in size and shape to the evidence recovery sheet. For convenience, the protective cover may be attached to the evidence recovery sheet. Typically, the protective cover will be attached to the evidence recovery sheet such that the cover and recovery sheet are substantially juxtaposed and coextensive along one side.

The protective cover and evidence recovery sheet may include at least one projecting tab, thereby improving ease of handling, for example when an investigator is required to place the protective cover over the evidence recovery sheet after evidence is recovered, or when the cover must be removed to recover and analyze evidence. The evidence recovery sheet or protective cover may also include a label surface for including with any desired information regarding the crime scene and the investigator, thereby cataloging the sheet for purposes of further investigation. The label surface may be integral with the evidence recovery sheet or protective cover, or may be provided as a separate evidence label as is known in the art.

The evidence recovery sheet may include at least one strip of a second adhesive. This adhesive strip is typically placed on a surface of the recovery sheet obverse to the low tack adhesive surface. It will be appreciated that this provides a means to prevent inadvertent dislodgement of the evidence recovery sheet from the floor surface on which it is placed. This second adhesive may have a relatively higher tack in comparison to the low tack adhesive, thereby reducing the risk of inadvertent dislodgement when the user lifts his or her foot.

It will be appreciated that for convenience, a plurality of evidence recovery units, comprising evidence recovery sheets and protective covers as described above, may be placed in a vertically stacked orientation. As each investigator passes through the entryway to a crime scene and steps on the top-most evidence recovery sheet, it may be removed, covered with a protective cover, and labeled with any desired information. In this way, evidence removed from the footwear of a particular investigator may be keyed to that investigator during further analysis.

Other objects and applications of the present invention will become apparent to those skilled in this art from the following description wherein there is shown and described a preferred embodiment of this invention, simply by way of illustration of the modes currently best suited to carry out the invention. As it will be realized, the invention is capable of other different embodiments and its several details are capable of modification in various, obvious aspects all without departing from the invention. Accordingly, the drawings and descriptions will be regarded as illustrative in nature and not as restrictive.

BRIEF DESCRIPTION OF THE DRAWING

The accompanying drawing incorporated in and forming a part of the specification illustrates several aspects of the present invention and, together with the description, serves to explain the principles of the invention. In the drawing.

Reference will now be made in detail to the presently preferred embodiments of the invention, examples of which are illustrated in the accompanying drawing.

DETAILED DESCRIPTION OF THE INVENTION

As summarized above, the present invention relates to novel methods and devices for collecting evidence inadvertently adhered to the footwear of persons passing through a crime scene. The methods and devices of the present invention may be accomplished by various means which are illustrated in the examples below. These examples are intended to be illustrative only, as numerous modifications and variations will be apparent to those skilled in the art.

Figure 1:
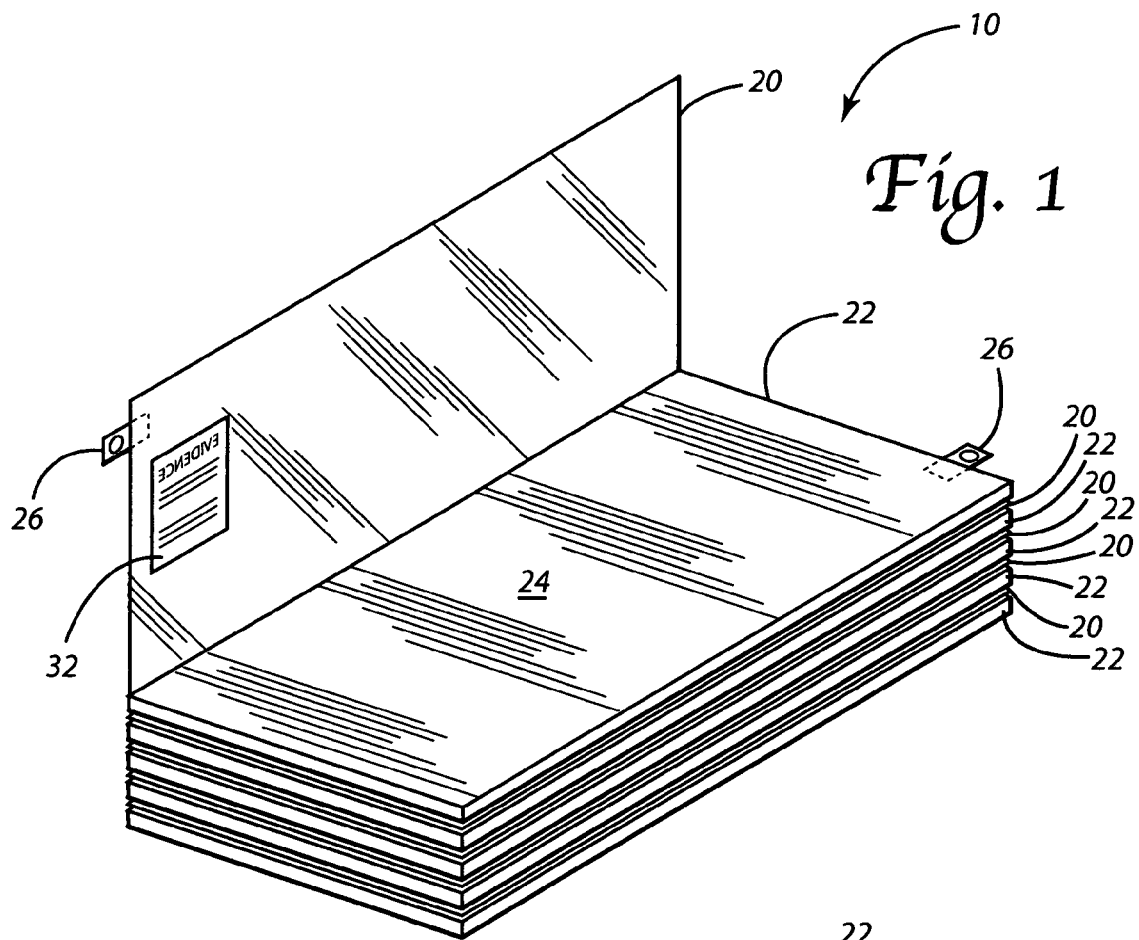
FIG. 1 shows the device for collecting crime scene evidence of the present invention.

Referring now to FIG. 1, in accordance with the method of the present invention, an evidence recovery unit 10 for recovering crime scene evidence from the footwear of personnel investigating the scene shown, comprising a cover sheet 20 and an evidence recovery sheet 22. The surface 24 of the evidence recovery sheet 22 facing cover sheet 20 is coated with any suitable low tack adhesive. Low tack adhesives, suitable for removing material from footwear contacting same but from which items adhered may be easily recovered, are known in the art. An example is low-tack adhesive label stock.

The cover sheet 20 may be transparent or opaque, and may be fabricated from any material capable of adhering to and being removed from the evidence recovery sheet 22 without damaging or removing evidence. Exemplary materials include wax paper, plastics, and the like. The cover sheet 20 may be separate from the evidence recovery sheet 22. Alternatively, the cover sheet 20 may be joined to the evidence recovery sheet 22 for convenience, typically such that the evidence recovery sheet and protective cover are substantially juxtaposed and coextensive along one side. The protective cover 20 and evidence recovery sheet 22 may be any desired shape, such as square, rectangular, octagonal, and the like, and may be of any desired dimension in accordance with the dimensions of the entryway near which they are to be placed.

Figure 2:
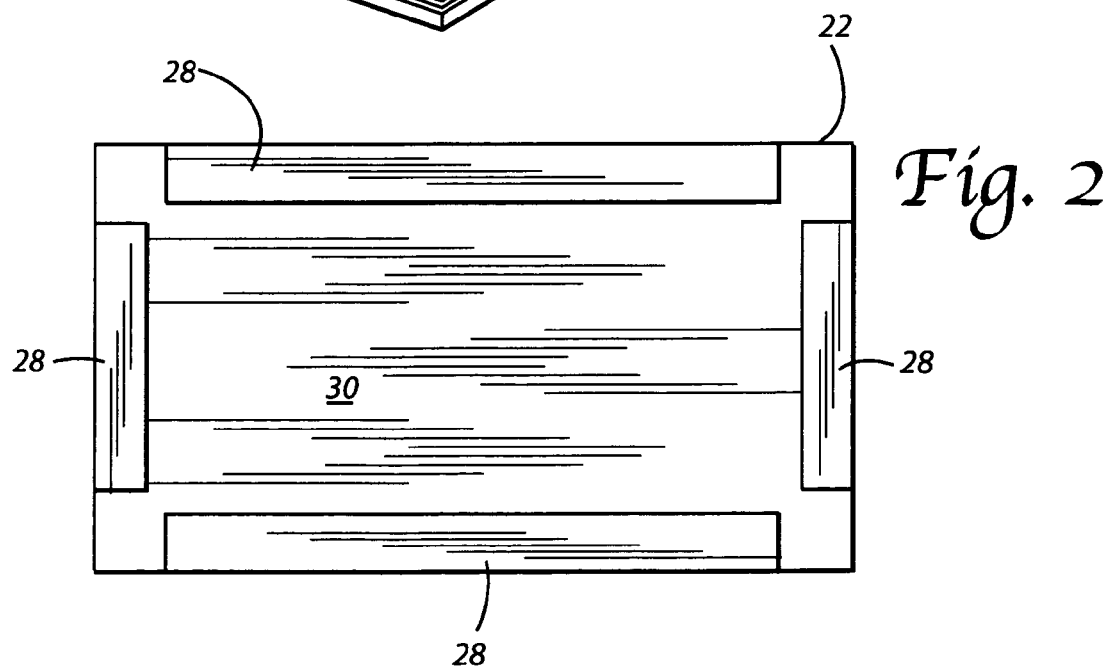
FIG. 2 shows the obverse side of the device of FIG. 1, including adhesive strips for temporarily affixing the device to a surface.

The protective cover 20 and evidence recovery sheet 22 may include projecting tabs 26 for ease of handling, e.g., when protective cover 20 and recovery sheet 22 are juxtaposed and/or separated. As shown in FIG. 2, the evidence recovery sheet 22 may also include at least one adhesive strip 28, placed on a surface 30 obverse to surface 24. It will be appreciated that adhesive strips 28, when placed in contact with, e.g., a floor surface in substantial proximity to an entryway to a crime scene, prevent inadvertent dislodgement of the evidence recovery sheet 22 from a desired location. Any suitable adhesive may be used for adhesive strip 28. The adhesive used on adhesive strip 28 may have a greater tack than the low tack adhesive covering surface 24 of evidence recovery sheet 22. It will be appreciated that this feature provides resistance against the inadvertent dislodgement of the evidence recovery sheet 22 when an individual attempts to lift his or her foot after stepping thereon. An example of a suitable material for adhesive strips 28 is double-sided tape having adhesive on two opposing surfaces, such tape being well known in the art.

A label 32 may be included in any desired location, such as on protective cover 20. Label 32 allows an investigator to include any desired information relating to the evidence and/or crime scene, such as a case number, an inventory number, a description of the type of crime, a description of the evidence, the location of the crime, information regarding the crime victim, and the chain of possession of the evidence adhered to the corresponding evidence recovery sheet 22. This type of information is crucial to the cataloging and preservation of evidence during an investigation. Label 32 may be integral, or a separate evidence label 32 having an adhesive backing may be used. Such labels are known in the art.

In another aspect, the device of the present invention may comprise a plurality of evidence recovery units 10 placed in a vertically stacked orientation. For convenience, a carrying case (not shown) of any suitable manufacture may be provided therefor. As will be described in greater detail below, this allows evidence recovered from the footwear of an individual investigator to be kept separate from evidence recovered from the footwear of other investigators.

A method of use of the invention will now be described. Typically, the evidence recovery unit 10 will be placed in at least one entryway to a crime scene, such as on the floor in substantial proximity to a door or window. Protective cover 20 is then removed or pulled back, exposing the low tack adhesive on surface 24 of evidence recovery sheet 22. As a crime scene investigator or other person exits the crime scene, he or she is required to place both feet on the surface 24 of evidence recovery sheet 22. Adhesive strips 28 prevent dislodgement of evidence recovery sheet 22 when the investigator steps off of the sheet 22. It will be appreciated that any evidence such as fibers, hairs, fluids, and the like inadvertently adhered to the investigator's footwear during the course of the investigation will be removed therefrom, and adhere to the low tack adhesive on surface 24.

The protective cover 20 may then be placed on evidence recovery sheet 22 such that substantially the entirety of surface 24, and any evidence adhered thereto, is covered. Any desired information regarding the investigator, crime scene, or evidence may then be recorded on label 32. The evidence recovery unit 10 may then be transported to, e.g., a crime laboratory. Any evidence adhered to surface 24 may then be removed, typically manually or by chemical means, and analyzed. Exemplary removal techniques include swabs, tweezers, scraping with a razor blade or scalpel, and the like. A second evidence recovery unit 10 may then be placed in the entryway, ready to collect evidence from the next investigator to pass therethrough.

It will be appreciated also that alternate means for keeping evidence collected from different investigators separately catalogued are possible. For example, use of a plurality of vertically stacked evidence recovery units 10 would also allow evidence collected from the footwear of an individual investigator to be preserved separately from evidence collected from the footwear of any subsequent investigator. The plurality of evidence recovery units 10 are placed in an entryway to a crime scene as described above. Evidence from the footwear of a first investigator adheres to the top-most evidence recovery unit 10, and the top-most evidence recovery unit 10 is sealed, labeled, and removed. In this manner, the next evidence recovery unit 10 is exposed, ready to collect evidence from the footwear of the next investigator to pass. The plurality of evidence recovery units 10 may be loosely stacked, or may be attached one to another by any suitable means, such as staples, binder rings, weak adhesives, and the like.

It should also be appreciated that the present invention provides also a method for preventing contamination of a crime scene. The evidence recovery unit 10 may be placed in substantial proximity to a crime scene entryway, and investigative personnel required to step thereon prior to entry into the crime scene. As noted above, the low tack adhesive of surface 24 of the evidence recovery sheet 22 will remove dirt and debris from the footwear of the personnel, in this case prior to entry into the crime scene. In this manner, the present invention provides a means for avoiding inadvertent contamination of a crime scene by, e.g., dirt and debris carried therein on the footwear of the investigators on the scene.

The foregoing description of preferred embodiments of the invention has been presented for purposes of illustration and description. It is not intended to be exhaustive or to limit the invention to the precise form disclosed. Obvious modifications or variations are possible in light of the above teachings. The embodiments were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

What is claimed is:

1. A method for recovering evidence from the footwear of personnel investigating a crime scene comprising the steps of:
   placing an evidence recovery sheet having a low tack adhesive on at least one surface thereof in substantial proximity to at least one entryway to said crime scene;
   causing said personnel to step on the evidence recovery sheet prior to exiting the crime scene, whereby any evidence carried on the personnel's footwear adheres to said recovery sheet;
   covering said evidence recovery sheet with a protective cover to preserve the integrity of evidence adhered thereto; and
   recovering said adhered evidence from the evidence recovery sheet.

2. The method set forth in claim 1, wherein said evidence recovery sheet includes a first surface and a second surface, said first surface including said low tack adhesive, and said second surface including at least one strip of a second adhesive, said second adhesive being of higher tack than said low tack adhesive to prevent inadvertent dislodgement of said evidence recovery sheet from its location.

3. The method set forth in claim 1, further including the step of recording desired information relating to the crime scene and/or the personnel on said evidence recovery sheet or said protective cover.

4. The method set forth in claim 1, including orienting a plurality of said evidence recovery sheets and protective covers in a vertically stacked relationship and placing said sheets and covers in substantial proximity to said entryway.

5. The method set forth in claim 4, further including the steps of removing the topmost evidence recovery sheet after an individual steps thereon, covering the evidence recovery sheet with the protective cover, and exposing the underlying evidence recovery sheet prior to contact with another individual.

6. A method for preventing contamination of a crime scene by personnel investigating said crime scene, comprising the steps of:
   placing an evidence recovery sheet having a low tack adhesive on at least one surface thereof in substantial proximity to at least one entryway to said crime scene; and
   causing said personnel to step on the evidence recovery sheet prior to entering the crime scene, whereby any dirt or debris carried on the personnel's footwear adheres to said recovery sheet.

7. A device for recovering evidence from the footwear of personnel investigating a crime scene, comprising a plurality of adhesive evidence recovery units placed in a vertically stacked orientation, each of said evidence recovery units comprising:
   an evidence recovery sheet having a low tack adhesive on at least one surface thereof; and
   a protective cover for preserving the integrity of evidence adhered to said evidence recovery sheet, said protective cover being similar in size and shape to said evidence recovery sheet;
   wherein the low tack adhesive and protective cover are placed on a topmost surface of the evidence recovery sheet.

8. The device of claim 7, wherein each adhesive evidence recovery unit includes a labeling surface for recording desired information thereon.

9. The device of claim 7, wherein said protective cover includes at least one projecting tab for ease of handling.

10. The device of claim 7, wherein said evidence recovery sheet includes at least one projecting tab for ease of handling.

11. The device of claim 7, wherein said evidence recovery sheet includes at least one strip of a second adhesive, said adhesive strip being placed on a surface of the recovery sheet obverse to the low tack adhesive surface.

12. The device of claim 11, wherein said second adhesive is of a relatively higher tack in comparison to said low tack adhesive.

13. The device of claim 7, wherein said protective cover is attached to said evidence recovery sheet.

14. The device of claim 13, wherein said protective cover is attached to said evidence recovery sheet such that the cover and recovery sheet are substantially juxtaposed and coextensive along one side.

* * * * *